United States Patent [19]

Tsunoda et al.

[11] 4,112,221

[45] Sep. 5, 1978

[54] PROCESS FOR PREPARING 8,2'-O-ANHYDROPURINE NUCLEOSIDES

[75] Inventors: Kozo Tsunoda; Tsuneo Sowa, both of Nobeoka; Kunio Iitsuka, Fuji; Kiyohide Sako, Nobeoka, all of Japan

[73] Assignee: Asahi Kasei Kogyo Kabushiki Kaisha, Osaka, Japan

[21] Appl. No.: 594,829

[22] Filed: Jul. 10, 1975

[30] Foreign Application Priority Data

Jul. 17, 1974 [JP] Japan .................................. 49-81171
Aug. 9, 1974 [JP] Japan .................................. 49-90716

[51] Int. Cl.$^2$ ........................................... C07H 19/16
[52] U.S. Cl. ........................................ 536/24; 536/26; 536/23
[58] Field of Search ................... 260/211.5 R; 536/24, 536/26

[56] References Cited

U.S. PATENT DOCUMENTS

| 3,322,747 | 5/1967 | Shen et al. ..................... 260/211.5 R |
| 3,792,040 | 2/1974 | Moffatt et al. ................. 260/211.5 R |
| 3,873,515 | 3/1975 | Sowa et al. ..................... 260/211.5 R |

OTHER PUBLICATIONS

Ikehara et al., "Tetrahedron", vol. 26, pp. 4251–4259, Pergamon Press, Great Britain, 1970.
Ogilvie et al., "Canadian Journal of Chem.", vol. 50, 1972, pp. 1100–1104.

*Primary Examiner*—Johnnie R. Brown
*Attorney, Agent, or Firm*—Burgess, Dinklage & Sprung

[57] ABSTRACT

Process for preparing 8,2'-O-anhydropurine nucleosides having a utility as intermediates for antiviral and anticarcinogenic drugs which comprises heating 2',3'-O-sulfinyl-8-oxypurine nucleosides in an aprotic polar solvent in the presence of an alkali metal, alkaline earth metal or ammonium salt of an inorganic or organic weak acid.

5 Claims, No Drawings

PROCESS FOR PREPARING 8,2'-O-ANHYDROPURINE NUCLEOSIDES

This invention relates to a new process for preparing a 8,2'-O-anhydropurine nucleoside.

More particularly, it is concerned with a new and improved process for preparing a 8,2'-O-anhydropurine nucleoside having the formula

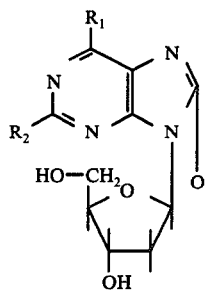

wherein $R_1$ and $R_2$ individually represent a hydrogen atom, hydroxy group, amino group, mercapto group or a halogen atom, starting from a 2',3'-O-sulfinyl-8-oxypurine nucleoside having the formula

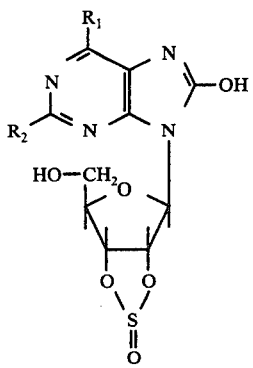

wherein $R_1$ and $R_2$ are as defined above.

The 8,2'-O-anhydropurine nucleosides (I) obtainable by the process of this invention are valuable compounds as intermediates for the synthesis of arabinofuranosylpurine nucleosides, which have antiviral and anticarcinogenic activities and thus a usefulness as a medicine, and a variety of other useful nucleic acid derivatives. For instance, the anhydropurine nucleosides (I) can be converted to arabinofuranosylpurine nucleosides having the formula

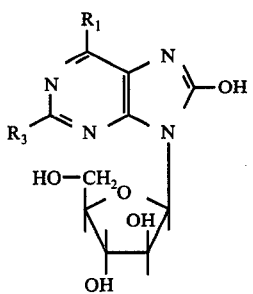

wherein $R_1$ and $R_2$ are as defined above, by treatment with hydrogen sulfide and subsequent desulfurization of the so obtained 8-mercapto compounds according to the method disclosed and claimed in Japanese Patent Publication No. 7271/1972, or by treatment with liquid hydrogen sulfide and subsequent reduction according to the method taught in Tetrahedron, 28, 3695 (1972). It is disclosed in Cancer, 64(5), 519 (1973) that the nucleosides (III) have antiviral and anticarcinogenic activities and may be useful as medicines.

For the production of the 8,2'-O-anhydropurine nucleosides, there has been heretofore proposed a method wherein an electron attractive group, e.g., p-toluenesulfonyl group, is introduced into the hydroxy group at the 2'-position in a 8-oxypurine nucleoside and then a 8,2'-O-anhydro linkage is formed simultaneously with elimination of said electron attractive group [See, Tetrahedron, 24, 3498 (1968) and Chemical & Pharmaceutical Bulletin, 18, 240 (1970)].

In the prior method, however, it is known that selective introduction of such electron attractive group into the hydroxy group at the 2'-position in the 8-oxypurine nucleoside encounters great difficulty, together with extremely complicated procedures and highly expensive reagents applied therein, and also that the desired 8,2'-O-anhydropurine nucleosides are obtained in a low yield. Therefore, such a prior method could not entirely be considered as commercially satisfactory.

As a result of our further studies, we have found and completed a new and improved process of this invention wherein the 8,2'-O-anhydropurine nucleosides (I) can be much more advantageously produced from the 2',3'-O-sulfinyl 8-oxypurine nucleosides (II).

It is, accordingly, a primary object of this invention to provide a new process for preparing the 8,2'-O-anhydropurine nucleosides which are valuable intermediates for medicine.

Other objects and advantages of this invention will be apparent from the following description.

According to the present invention, there is provided a process for the preparation of a 8,2'-O-anhydropurine nucleoside of the formula (I) which comprises heating a 2',3'-O-sulfinyl 8-oxypurine nucleoside of the formula (II) in an aprotic polar solvent in the presence of an alkali metal, alkaline earth metal or ammonium salt of a weak acid.

The starting material in the method of this invention, namely a 2',3'-O-sulfinyl 8-oxypurine nucleoside of the formula (II) may be easily prepared, for example by a method disclosed in Japanese Patent Application Laid-Open to Public No. 49-61196.

In carrying out the process of this invention, the reaction can be easily effected by heating a 2',3'-O-sulfinyl 8-oxypurine nucleoside in a suitable aprotic polar solvent in the presence of the above-mentioned salt.

The "aprotic polar solvent" which may be used in the process of this invention is meant to include a dialkyl sulfoxide, e.g., dimethyl sulfoxide, a dialkyl-formamide, e.g., dimethylformamide; and a hexaalkylphosphoramide, e.g., hexamethylphosphoramide. The amount of said solvent to be employed in this reaction is usually in a range of 5 l. or more with respect to one mole of the starting nucleoside (II) and preferably to 20 to 50 l. However, an excessively large amount of said solvent is not economically advantageous, though such an amount does not adversely affect the reaction proceeding to the 8,2'-O-anhydropurine nucleoside (I).

The alkali metal, alkaline earth metal or ammonium salts of weak acids which are employed in this reaction, are believed to act as a reaction accelerator for the reaction in forming the 8,2'-O-anhydropurine nucleoside (I) from the 2′,3′-O-sulfinyl 8-oxypurine nucleoside (II). The weak acids which may be employed in their salt forms in this reaction, are preferably those showing a pH of higher than 4 when their salts are dissolved in water. Representative examples of the weak acids may include an inorganic weak acid, e.g., carbonic acid, bicarbonic acid, boric acid, sulfurous acid, bisulfurous acid, phosphoric acid, nitrous acid, hydroiodic acid; and an organic weak acid, e.g., acetic acid, formic acid, oxalic acid, propionic acid, butyric acid, tartaric acid, citric acid, adipic acid, glutamic acid, benzoic acid, phthalic acid, p-aminobenzoic acid, salicylic acid. The alkali metals and alkaline earth metals which may be employed in forming the corresponding weak acid salts may include sodium, potassium, calcium, barium, etc. Representative examples of said salts may be illustrated as given below.

Sodium hydrogencarbonate, potassium hydrogencarbonate, potassium borate, barium borate, sodium hydrogensulfite, calcium sulfite, potassium phosphate, disodium hydrogenphosphate, sodium nitrite, sodium iodide. Sodium acetate, ammonium acetate, lithium acetate, sodium formate, potassium propionate, calcium butyrate, sodium tartrate, barium tartrate, sodium adipate, potassium hydrogenglutamate, sodium citrate, potassium hydrogenphthalate, sodium benzoate, potassium benzoate, sodium p-aminobenzoate, potassium salicylate. These salts may be favorably employed in this reaction either alone or in combination. The amount of the salt to be added is usually in a range of equimolar or more with respect to one mole of the starting 2′,3′-O-sulfinyl-8-oxypurine nucleoside (II) and preferably of 1.5 to 10 moles. In case a lower amount of the salt is added than is required, the yield of the desired 8,2′-O-anhydropurine nucleoside (I) is extremely lowered. In case no salt is added, the present reaction hardly proceeds. It is to be noted that an amount more than that required is not desirable, since such an amount is not only of no ecconomical significance but also of no usefulness in the present reaction as well as isolation and purification of the desired nucleoside.

Reaction temperature in the present reaction is usually within a range of not less than 80° C. and preferably of 80° C. to 160° C. Reaction period of time may vary depending upon other conditions such as reaction temperature, reagents' concentrations, the kind and amount of the reaction accelerator (alkali metal, alkaline earth metal or ammonium salt of a weak acid), etc., but it usually and advantageously takes 1–10 hours. It is noted that extremely prolonged reaction period and high reaction temperature is not desirable, as they tend to enhance formation of by-products, with various decomposition reactions of the starting material and product.

After completion of the reaction, the desired nucleoside (I) may be easily recovered and purified from the reaction mixture in a conventional manner, for example, by concentrating the reaction mixture under reduced pressure, mixing the concentrate with a suitable amount of water and subsequently crystallizing or adsorption on a suitable ion exchange resin for separation of concomitant impurities, eluting with a suitable eluent and concentrating for crystallization.

This invention will be more fully illustrated by the following examples, but these examples are not to be construed as limiting the scope of this invention.

EXAMPLE 1

In 500 ml. of dimethylformamide there was dissolved with stirring 4.95 g. (15 mmol.) of 2′,3′-O-sulfinyl-8-oxyadenosine hydrochloride and then 3.69 g. (45 mmol.) of sodium acetate was added thereto. The resulting mixture was heated to 115° C. for 3 hours. The reaction mixture (yield of 8,2′-O-anhydroadenosine: 85.3%) was concentrated at 90° C. under reduced pressure to about 10 ml. and 100 ml. of water was mixed with the concentrate. The resulting mixture was allowed to stand at 5° C. with stirring overnight. Crystalline substance separated out in situ was collected by filtration, washed with cold water and then dried at 60° C. under reduced pressure to give 2.4 g. of 8,2′-O-anhydroadenosine.one-half $H_2O$ (purity: 99.0%) as crystals.

Analysis (%) Found, C: 43.6, H: 4.50, N: 24.9 Calculated, C: 43.8, H: 4.38, N: 25.5 m.p. 201°–202° C. $\lambda_{max}^{pH2}$ 259 nm

EXAMPLE 2

In 250 ml of dimethyl sulfoxide there was dissolved with stirring 3.3 g. (10 mmol.) of 2′,3′-O-sulfinyl-8-oxyadenosine hydrochloride and then 8.0 g. (50 mmol.) of potassium benzoate was added thereto. The resulting mixture was heated to 140° C. for 1 hour. The reaction mixture (yield of 8,2′-O-anhydroadenosine: 74.7%) was worked up in the same manner as in Example 1 to give 1.8 g. of 8,2′-O-anhydroadenosine.one-half $H_2O$ (purity: 97.2%) as crystals.

EXAMPLE 3

Following the same procedures as in Example 1 except that 12.3 g. (60 mmol.) of potassium hydrogenphthalate was used instead of the sodium acetate, there was obtained 2.0 g. of 8,2′-O-anhydroadenosine one-half $H_2O$ (purity: 96.5%) as crystals.

EXAMPLE 4

Following the same procedures as in Example 1 except that 700 ml. of hexamethylphosphoramide was used instead of the dimethylformamide, there was obtained 1.9 g. of 8,2′-O-anhydroadenosine.one-half $H_2O$ (purity: 98.4%) as crystals.

EXAMPLE 5

Following the same procedures as in Example 1 except that 14.4 g. (100 mmol.) of sodium benzoate was used instead of the sodium acetate, there was obtained 1.9 g. of 8,2′-O-anhydroadenosine.one-half $H_2O$ (purity: 96.6%) as crystals.

EXAMPLE 6

In 300 ml. of dimethylformamide there was dissolved with stirring 3.30 g. (10 mmol.) of crystalline 2′,3′-O-sulfinyl-8-oxyadenosine hydrochloride and then 2.52 g. (30 mmol.) of sodium hydrogencarbonate was added thereto. The resulting mixture was heated to 110° C. for 3 hours. The reaction mixture (yield of 8,2′-O-anhydroadenosine: 85.6%) was concentrated at 90° C. under reduced pressure to about 10 ml. and 100 ml. of water was mixed with the concentrate. The resulting mixture was allowed to stand at 5° C. with stirring overnight. Crystalline substance separated out in situ was collected by filtration, washed with cold water and then dried at 60° C. under reduced pressure to give 1.82 g. of 8,2′-O-anhydroadenosine.one-half $H_2O$ (purity: 98.5%) as white crystals.

Analysis (%) Found, C: 43.1, H: 4.42, N: 24.6 Calculated, C: 43.8, H: 4.38, N: 25.5 m.p. 198°–202° C. (dec.) $\lambda_{max}^{pH2}$ 259 nm

EXAMPLE 7

In 200 ml. of dimethyl sulfoxide there was dissolved with stirring 3.14 g. (10 mmol.) of crystalline 2',3'-O-sulfinyl-8-oxyinosine and then 2.05 g. (25 mmol.) of sodium acetate was added thereto. The resulting mixture was heated to 130° C. for 2 hours. The reaction mixture (yield of 8,2'-O-anhydroinosine: 79.2%) was subjected to distillation under reduced pressure at 90° C. to recover the dimethyl sulfoxide and then the residue was dissolved in 1 l. of water. The resulting solution was supplied to a column which was packed with 200 ml. of a strongly basic ion exchange resin, Amberlite IRA-900 (Trade name, available from Rohm & Haas Co., U.S.A., $CH_3COO^-$ form). After thoroughly washing the column with water, gradient elution of the 8,2'-O-anhydorinosine adsorbed on the column was effected with 0.2 N aqueous acetic acid solution. The effluents containing the anhydroinosine were concentrated under reduced pressure and the concentrate was left with stirring in a cold place at 5° C. overnight. Crystalline substance separated out in situ was collected by filtration and dried to give 1.70 g. of 8,2'-O-anhydroinosine (purity of 99.2%) as white crystals.

Analysis (%) Found, C: 42.5, H: 4.11, N: 19.6 Calculated, C: 42.3, H: 4.23, N: 19.7 m.p. 182° C. (dec.) $\lambda_{max}^{pH2}$ 251 nm, 275 nm (sh.)

EXAMPLE 8

In 500 ml. of dimethyl sulfoxide there was dissolved with stirring 3.66 g. (10 mmol.) of crystalline 2',3'-O-sulfinyl-8-oxyguanosine hydrochloride and then 8.00 g. (50 mmol.) of potassium benzoate was added thereto. The resulting mixture was heated to 145° C. for 2 hours. The reaction mixture (yield of 8,2'-O-anhydroguanosine: 80.3%) was worked up in the same manner as in Example 2 to give 2.01 g. of 8,2'-O-anhydroguanosine (purity of 98.7%) as white crystals.

Analysis (%) Found, C: 39.5, H: 4.41, N: 24.0 Calculated, C: 40.2, H: 4.35, N: 23.4 m.p. > 173° C. (dec.) $\lambda_{max}^{pH2}$ 247 nm, 286 nm

EXAMPLE 9

In 200 ml. of hexamethylphosphoramide there was dissolved with stirring 3.49 g. (10 mmol.) of 2',3'-O-sulfinyl-8-oxy-6-chloroinosine and then 2.94 g. (30 mmol.) of potassium hydrogencarbonate was added thereto. The resulting mixture was heated to 105° C. for 6 hours. The reaction mixture (yield of 8,2'-O-anhydro 6-chloroinosine: 77.9%) was concentrated to dryness under reduced pressure and the residue was dissolved in 1 l. of water. The resulting solution was supplied to a column of 200 ml. of a strongly basic ion exchange resin, Amberlite-900 (Trade name, available from Rohm & Haas Co., borate form), which was then eluted with 0.5 mole boric acid solution. The effluents containing 8,2'-O-anhydro 6-chloroinosine were collected by filtration and passed through 100 ml. of granular active charcoal, Adostar, (Trade name, available from Adosto Kasei K.K., Japan) to absorb 8,2'-O-anhydro-6-chloroinosine thereon. After washing with 600 ml. of water, elution was effected with 2% ammonia and 30% aqueous methanol. The eluates were concentrated to substantial dryness at a temperature of 30° C. or lower and the concentrate was allowed to stand with stirring for 48 hours. Crystalline substance separated out was collected by filtration and then dried to give 1.64 g. of 8,2'-O-anhydro-6-chloroinosine (purity of 98.1%).

Analysis (%) Found, C: 38.9, H: 3.40, N: 18.7, Cl: 11.1 Calculated, C: 39.5, H: 3.31, N: 18.5, Cl: 11.7 m.p. > 253° C. (dec.) $\lambda_{max}^{pH2}$ 255 nm, 277 nm

EXAMPLE 10

In 250 ml. of dimethylformamide there were dissolved with stirring 3.46 g. (10 mmol.) of 2',3'-O-sulfinyl-8-oxy 6-mercaptoinosine and 4.41 g. (15 mmol.) of sodium citrate dihydrate and the resulting mixture was heated to 110° C. for 4 hours. The reaction mixture (yield of 8,2'-O-anhydro 6-mercaptoinosine: 81.3%) was worked up in the same manner as in Example 1 to give 1.81 g. of 8,2'-O-anhydro 6-mercaptoinosine (purity of 98.0%) as crystals.

Analysis (%) Found, C: 39.7, H: 3.58, N: 19.0, S: 10.2 Calculated, C: 40.2, H: 3.68, N: 18.8, S: 10.7 m.p. > 174° C. (dec.)

EXAMPLE 11

Following the same procedures as in Example 2 except that 3.45 g. (50 mmol.) of sodium nitrite was used instead of the sodium acetate, there was obtained 1.57 g. of 8,2'-O-anhydroinosine (a purity of 98.3%).

EXAMPLE 12

In 500 ml. of dimethylacetamide there was dissolved with stirring 3.30 g. (10 mmol.) of crystalline 2',3'-O-sulfinyl 8-oxyadenosine hydrochloride and 2.20 g. of dilithium hydrogenphosphate was added thereto. The resulting mixture was heated to 130° C. for 2 hours. The reaction mixture (yield of 8,2'-O-anhydroadenosine: 77.8%) was worked up in the same manner as in Example 1 to give 1.45 g. of 8,2'-O-anhydroadenosine (purity of 97.6%) as crystals.

EXAMPLES 13 to 25

The reaction was effected in the same manner as in Example 1 except that a weak acid salt indicated in the following Table was used instead of the sodium hydrogencarbonate. Yields of 8,2'-O-anhydroadenosine in the Examples are also shown in the Table.

Table

| Ex. | Weak acid salt | Added amount [g (mmol)] | Yield of 8,2'-O-anhydro-adenosine (%) |
|---|---|---|---|
| 13 | Potassium borate | 6.26 (20) | 85.0 |
| 14 | Ammonium acetate | 3.85 (50) | 77.4 |
| 15 | Potassium hydrogenadipate | 5.52 (30) | 83.6 |
| 16 | Sodium formate | 2.72 (40) | 66.9 |
| 17 | Calcium butyrate | 2.52 (20) | 74.9 |
| 18 | Potassium dihydrogenphosphate | 4.76 (35) | 68.3 |
| 19 | Dipotassium hydrogenphosphate | 4.35 (25) | 72.8 |
| 20 | Sodium phosphate | 2.16 (15) | 65.2 |
| 21 | Calcium sulfite | 2.40 (20) | 52.7 |
| 22 | Potassium hydrogensulfite | 2.40 (30) | 70.1 |
| 23 | Sodium iodide | 9.00 (60) | 53.7 |
| 24 | Barium tartrate | 8.55 (30) | 61.8 |
| 25 | Lithium acetate | 1.98 (30) | 76.4 |

EXAMPLE 26

In 250 ml. of dimethylformamide there was dissolved with stirring 4.00 g. (10 mmol.) of 2',3'-O-sulfinyl-8-oxy-2-chloroadenosine hydrochloride and then 5.00 g. (50 mmol.) of potassium acetate was added thereto. The resulting mixture was heated to 110° C. for 3 hours. The reaction mixture was worked up in the same manner as in Example 4 to give 1.76 g. of 8,2'-O-anhydro-2-chloroadenosine (purity of 98.0%) as white crystals.

EXAMPLE 27

Following the same procedures as in Example 4 except that 4.00 g. (10 mmol.) of 2',3'-O-sulfinyl-8-oxy-6-chloroguanosine hydrochloride was used instead of the 2',3'-O-sulfinyl 8-oxy-6-chloroinosine, there was obtained 1.83 g. of 8,2'-O-anhydro 6-chloroguanosine (purity of 97.2%) as white crystals.

EXAMPLE 28

In 500 ml. of dimethylformamide there was dissolved with stirring 4.92 g. (10 mmol.) of 2',3'-O-sulfinyl-8-oxy-2-iodoadenosine hydrochloride and 6.40 g. (40 mmol.) of potassium hydrogenphthalate was added thereto. The resulting mixture was heated to 105° C. for 4 hours. The reaction mixture was worked up in the same manner as in Example 4 to give 2.76 g. of 8,2'-O-anhydro-2-iodoadenosine (purity of 97.7%) as white crystals.

EXAMPLE 29

A suspension of 3.14 g. (10 mmol.) of 2',3'-O-sulfinyl-8-oxynebularin and 4.80 g. of potassium hydrogencarbonate in 200 ml. of dimethyl sulfoxide was heated to 120° C. with stirring for 3 hours. The reaction mixture was worked up in the same manner as in Example 1 to give 1.56 g. of 8,2'-O-anhydronebularin (purity of 96.9%) as white crystals.

What is claimed is:

1. A process for preparing a 8,2'-O-anhydropurine nucleoside having the formula

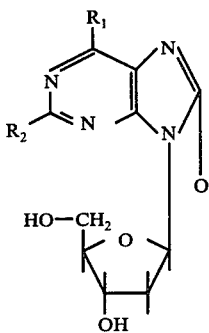

wherein $R_1$ and $R_2$ individually represent a hydrogen atom, hydroxy group, amino group, mercapto group or a halogen atom which comprises heating at a temperature from about 80° to 160° C. a 2',3-O-sulfinyl-8-oxypurine nucleoside having the formula

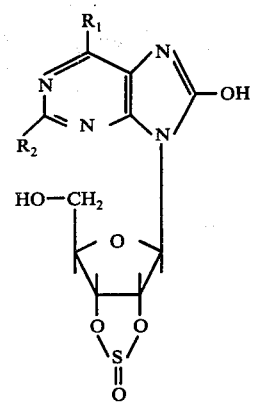

wherein $R_1$ and $R_2$ are as defined above in an aprotic polar solvent in the presence of salt selected from the group consisting of sodium hydrogencarbonate, potassium hydrogencarbonate, potassium borate, barium borate, sodium hydrogensulfite, calcium sulfite, potassium phosphate, disodium hydrogenphosphate, sodium nitrite, sodium iodine, sodium acetate, ammonium acetate, lithium acetate, sodium formate, potassium propionate, calcium butyrate, sodium tartrate, barium tartrate, sodium adipate, potassium hydrogenglutamate, sodium citrate, potassium hydrogenphthalate, sodium benzoate, potassium benzoate, sodium p-aminobenzoate and potassium salicylate.

2. A process according to claim 1 wherein said aprotic polar solvent is a dialkyl sulfoxide, a dialkylformamide or a hexaalkylphosphoramide.

3. A process according to claim 2 wherein said aprotic polar solvent is dimethyl sulfoxide, dimethylformamide or hexamethylphosphoramide.

4. A process according to claim 1 wherein said aprotic polar solvent is employed in an amount of 5 l. or more with respect to one mole of said 2',3'-O-sulfinyl-8-oxypurine nucleoside.

5. A process according to claim 1 wherein said alkali metal, alkaline earth metal or ammonium salt of a weak acid is employed in an amount of equimolar or more with respect to one mole of said 2',3'-O-sulfinyl-8-oxypurine nucleoside.

* * * * *